United States Patent [19]

Thompson

[11] Patent Number: 5,702,682
[45] Date of Patent: Dec. 30, 1997

[54] METHODS FOR PREPARING RADIOPAQUE MEDICAL DEVICES

[75] Inventor: Samuel Anthony Thompson, Wilmington, Del.

[73] Assignee: Hercules Incorporated, Wilmington, Del.

[21] Appl. No.: 566,452

[22] Filed: Dec. 1, 1995

[51] Int. Cl.⁶ ................................................. A61K 49/04
[52] U.S. Cl. .............................. 424/9.42; 424/900
[58] Field of Search ............................. 424/9.42, 900

[56] References Cited

U.S. PATENT DOCUMENTS

| | | | |
|---|---|---|---|
| 1,918,884 | 7/1933 | Zellmann | 424/9.42 |
| 4,239,113 | 12/1980 | Gross et al. | 206/568 |
| 4,346,216 | 8/1982 | Hinckley | 56/121 |
| 4,882,392 | 11/1989 | Smid et al. | 515/330.2 |
| 5,019,370 | 5/1991 | Jay | 424/4 |
| 5,024,232 | 6/1991 | Smid et al. | 128/654 |
| 5,318,768 | 6/1994 | Illig et al. | 424/5 |
| 5,352,431 | 10/1994 | Hashiguchi et al. | 424/4 |
| 5,405,600 | 4/1995 | Illig et al. | 424/5 |

FOREIGN PATENT DOCUMENTS 0645150   3/1995   European Pat. Off. .

*Primary Examiner*—Gary E. Hollinden
*Attorney, Agent, or Firm*—Martin F. Sloan

[57] ABSTRACT

Disclosed is a method for providing radiopacity to a medical device comprising incorporating in said medical device metal-cation salt of anionic polymer, wherein the metal has atomic weight greater than about 40; radiopaque medical devices comprising the essentially water-insoluble metal-cation salts of anionic polymers; and a method for carrying out x-ray diagnostic procedures comprising administering to a subject a contrast agent comprised of the essentially water-insoluble metal-cation salts of anionic polymer.

24 Claims, No Drawings

METHODS FOR PREPARING RADIOPAQUE MEDICAL DEVICES

FIELD OF THE INVENTION

This invention relates to a process for providing radiopacity to medical devices and to the devices with radiopacity.

BACKGROUND OF THE INVENTION

Medical devices for insertion into and use in the body often need to be substantially radiopaque in order allow observation of the device in vivo by x-ray radiography. When these medical devices are constructed of materials lacking sufficient inherent radiopacity, such as most organic polymers, the devices are often filled with heavy metal compounds to provide radiopacity. These heavy metal compounds are usually added in the form of finely divided crystalline inorganic salts, e.g. barium sulfate, bismuth subcarbonate, during processing of the material for construction of the medical device. This method is acceptable in applications where the device is removed essentially intact from the body. However, when medical devices are designed to degrade in vivo, the release of these crystalline fillers may lead to medical complications such as foreign body reactions, granuloma, fibrosis, metal toxicity, carcinoma, sarcoma, and stone formation.

Heavy metal compounds are also utilized for direct administration to humans and animals in order to improve the x-ray radiation absorption of different parts of the body such as cavities and soft tissues of various organs and blood vessels. In this application the heavy metal compounds are conventionally referred to as "contrast agents" or "imaging agents".

In U.S. Pat. No. 5,019,370 there is disclosed a biodegradable, particulate radiographic contrast medium which comprises biodegradable polymeric spheres of estimated average molecular weight of about $10^5$ to $10^7$ daltons and average diameter of about 10–1,000 nanometers and carrying at least one radiographically opaque element. The radiographically opaque elements are stated to be iodine, bromine, samarium, erbium and other lanthanides. The radiographically opaque elements are not ionic.

U.S. Pat. Nos. 4,882,392 and 5,024,232 disclose radiopaque complexes comprising heavy metal radiopacifying salts homogeneously distributed throughout the polymer. The radiopaque materials are comprised of heavy metal Lewis acid radiopacifying salts complexed with a polymer containing a Lewis base monomer.

In U.S. Pat. Nos. 5,318,768 and 5,405,600 there are disclosed compositions for coating the gastrointestinal tract of mammals to form a radiopaque coating thereon. The compositions comprise: an x-ray contrasting agent, a polymeric material which is at least partially water soluble and contains polarizable or ionizable groups, and a divalent metal ion selected from the group consisting of $Mg^{++}$, $Ca^{++}$, $Zn^{++}$ and $Ba^{++}$, which causes the polymeric material to form a film on the mucosa of the GI tract. The disclosed contrast agents do not contain metal cations.

The stated object of the invention disclosed in U.S. Pat. No. 5,352,431 is to provide an imaging agent for diagnosis having a suitable retention time in blood. The invention teaches the use of a water-soluble imaging agent comprising a chitosan oligosaccharide or a galactosamino oligosaccharide wherein the number of repeating monosaccharides is from 3 to 6 and wherein at least one of the —H groups is substituted with a bifunctional ligand, coordinated with a metal ion having an atomic number of 21–29, 31, 32, 37–39, 42–44, 49, and 56–83.

U.S. Pat. No. 4,346,216 discloses water-soluble complexes of osmium compounds with carbohydrates, which may be intravenously administered to mammals as x-ray contrast agents. The complexes may also be compounded with conventional pharmaceutical carriers.

European Patent Application, Publication No. 0 645 150 Al discloses medical devices and method of making medical devices comprising ionically crosslinked polymer.

SUMMARY OF THE INVENTION

This invention is a method for providing radiopacity to a medical device comprising:

(a) providing: (i) a medical device comprising a cation salt of an anionic polymer, and (ii) an aqueous solution of a water-soluble composition containing metal-cations of atomic weight greater than about 40; and (b) soaking said medical device in said aqueous solution for a time effective to replace at least a portion of the cations in the cation salt of anionic polymer with said metal-cations, to form an essentially water-insoluble, metal-cation salt of anionic polymer dispersed within said medical device, thereby obtaining a medical device with increased radiopacity.

In another embodiment the invention pertains to a method for making a medical device or component of a medical device with enhanced radiopacity comprising:

(a) providing: (i) water-insoluble metal-cation salt of artionic polymer, wherein the atomic weight of the metal-cation is greater than about 40, and (ii) moldable or extrudable polymer suitable for making a medical device;

(b) mixing the water-insoluble metal-cation salt of anionic polymer and moldable or extrudable polymer to obtain a mixture; and (c) molding or extruding the mixture to obtain a medical device or component of a medical device with enhanced radiopacity.

In yet another embodiment the invention is a method for carrying out an x-ray diagnostic procedure comprising: (a) administering to a subject a contrast agent comprised of an essentially water-insoluble metal-cation salt of anionic polymer, wherein the metal has an atomic weight greater than about 40; and (b) performing the x-ray diagnostic procedure on said subject.

DETAILED DESCRIPTION OF THE INVENTION

The present invention is a method for providing radiopacity to a medical device without the use of crystalline inorganic fillers, comprising incorporating in the medical device essentially water-insoluble metal-cation salt of anionic polymer wherein the metal has an atomic weight greater than about 40. The invention is particularly useful in applications where crystalline inorganic fillers might be set free in the body during service or degradation of the medical device.

Examples of typical medical devices for which the invention is applicable are: catheters, stents, cannulas, plugs and constrictors. Typical applications for these devices include urological and gastrointestinal applications such as uretheral, uretheral, bilial, ileal and pyloric stems. The devices of this invention are also useful in cardiovascular, lymphatic, neurological, integumental, skeletal, optical, nasal, oral, anal and vaginal applications. This invention would find utility in any application where x-ray observation of an implanted device is required.

The term "anionic polymer" is used herein to refer to polymers which are anionic in both their fully or partially ionized condition. For convenience the term is also used to describe the same polymers in their ionized or non-ionized state.

Anionic polymers for use in this invention comprise both natural and synthetic anionic polymers. Preferred anionic polymers are those that contain carboxylate or sulfate functionality, and polysaccharides that contain carboxylate or sulfate functionality are particularly preferred. Examples of natural anionic polymers that may be utilized in the invention are: alginic acid, pectinic acid, hyaluronic acid, heparin, heparin sulfate and chondroitin sulfate. Examples of synthetic anionic polymers are: polyacrylic acid, polymethacrylic acid, carboxymethyl cellulose, carboxymethyl cellulose, carboxymethyl dextran, carboxymethyl starch, carboxymethyl chitosan and carboxymethyl starch. The most preferred anionic polymer for use in the invention is alginic acid.

The number of repeating units in the anionic polymer preferably is greater than about 6. More preferably the number of repeating units is greater than about 10, and most preferably greater than about 25.

The first embodiment of this invention comprises imparting radiopacity to a medical device containing cation salt of anionic polymer by replacing at least a portion of the cations with metal-cations of atomic weight greater than about 40, to form essentially water-insoluble metal-cation salt of anionic polymer dispersed within the device. The replacement is accomplished by soaking the device in an aqueous solution of a composition containing said metal-cations.

The medical devices that are preferred for the practice of this embodiment are those that comprise cation salts of anionic polymers, such as those described in European Patent Application, Publication No. 0 645 150 A1, which is incorporated herein by reference in its entirety.

To achieve radiopacity by the methods of this invention, it is not necessary that the entire medical device be constructed of metal-cation salt of anionic polymer. It is sufficient that components or portions of the medical device contain metal-cation salt of anionic polymer.

The compositions containing metal-cations are preferably water-soluble salts of metal-cations with atomic weight greater than about 40. The term "metal" is defined in the conventional way as all elements with the exclusion of hydrogen, the inert gases, the halogens, boron, carbon, silicon, nitrogen, phosphorus, arsenic, oxygen, sulfur, selenium and tellurium.

Metal-cations with atomic weight greater than about 40 have been found to impart substantial radiopacity to medical devices. Preferred are metal-cations or mixtures of metal-cations from metals with atomic weight equal to or greater than about 87, and most preferred are metal-cations or mixtures of metal-cations from metals with atomic weight equal to or greater than about 137.

Preferred metal-cations for use in the invention are barium, strontium, iron, copper, lead, tin, iron, gold and silver cations. More preferred metal-cations are those from barium, strontium and lead, and the most preferred metal-cation is that from barium. Any essentially water-insoluble polymer/metal-cation salt made utilizing the metal-cations and anionic polymers described herein can be used in the practice of the invention. A particularly preferred metal-cation salt of anionic polymer is the barium salt of alginic acid.

In the practice of this invention metal-cation salt of anionic polymer may be used in the medical device at any level effective to achieve a desired degree of radiopacity. The degree of radiopacity observed depends not only on the identity of the radiopacifier used, but also on the amount of radiopacifier utilized, the size of the medical device and its location within the body. It is preferred that the minimum level of radiopacifier be about 1% on a dry weight basis based on the dry weight of the medical device. A more preferred minimum level is about 10%, and the most preferred minimum level is about 50%.

The second embodiment of this invention is a method for making medical devices or components of medical devices with enhanced radiopacity by mixing essentially water-insoluble metal-cation salt of anionic polymer, wherein the atomic weight of the metal-cation is greater than about 40, with a moldable or extrudable polymer suitable for producing medical devices, and then molding or extruding the mixture to form the medical device or component of a medical device. This embodiment is particularly useful as an alternative to incorporating crystalline inorganic fillers for providing radiopacity to medical devices.

Exemplary moldable or extrudable polymers used to manufacture medical devices or components of medical devices are: polyorthoesters, polycarbonates, polylactones, polyanhydrides, polyurethanes, polysulfones, polyether ketones and polysiloxanes.

Although this invention, in both of the embodiments discussed thus far, finds its primary utility where medical devices degrade naturally during service or are caused to degrade by application of a trigger for degradation, it may also be used as an alternative to crystalline inorganic fillers for providing radiopacity to non-degrading medical devices, i.e. those that do not degrade during service in vivo. Exemplary polymers that are used to manufacture non-degrading medical devices are: polyurethanes, polysulfones, polyether ketones and polysiloxanes.

Preparation of essentially water-insoluble metal-cation salts of anionic polymers for incorporation into medical devices is readily accomplished by adding an aqueous solution of a water-soluble salt of anionic polymer, e.g. an alkali metal salt, to an aqueous solution of water soluble salt of metal-cation. The water-insoluble metal-cation salt of anionic polymer precipitates as a solid or a hydrogel, either of which can be dried by conventional methods to yield a dry water-insoluble metal-cation salt of anionic polymer. This material may then be added in an effective mount to the particulate or pelleted polymeric material for manufacturing the medical device before it is molded or extruded into the device form.

Determination of the radiopacity of materials and devices may be carried out by Computed Tomography (CT) using procedures well known in the art. The units of radiopacity are hounsfield units, which are units of x-ray attenuation used for CT scans, each pixel being assigned a value on a scale where air=−1000, water=0, and compact bone=1000.

For the purposes of this invention, the preferred minimum level of radiopacity to be achieved in a medical device of this invention is about 100 hounsfield units. A more preferred minimum level of radiopacity is about 300 hounsfield units. An even more preferred level is about 500 hounsfield units, and the most preferred minimum level is about 700 hounsfield units.

When medical devices containing the essentially water-insoluble metal salts of anionic polymers of this invention degrade in vivo, the stability of the metal/polymer salt to body fluids will depend upon the level of contact with the body fluids, the selectivity of the polymer for the metal, the metal sequestering power of the solutes in the body fluid, and the part of the body in which the device is implanted. Devices located in exit systems, such as the urogenital or gastrointestinal systems may simply degrade and then release the metal-polymer salt, which then exits the body intact in the flow of excrement.

The metal sequestering power of the solutes in the body fluid is a function of the concentration of the metal binding solutes in the fluid, the metal binding strength of these solutes, the solubility of the solute-metal complex, and the availability of active solute. Upon degradation of the medical device in vivo, contact of the metal-polymer salt with body fluid having sufficient sequestrant power may result in the degradation of the metal/polymer salt with the concomitant formation of metal-sequestrant compounds. These newly formed compounds may be soluble or insoluble in body fluids depending upon the exact compounds formed. Insoluble compounds may remain supersaturated in the body fluids, or precipitate out to form extremely fine crystals. The soluble compounds and the fine crystalline compounds will be disposed of by the body using normal pathways for removal of waste. Even when fine crystalline compounds are produced, there is still a significant benefit in this invention over the use of crystalline filler for radiopacity because of the fine nature of the precipitate and its slow generation over time.

In its third embodiment this invention encompasses a method for carrying out an x-ray diagnostic procedure comprising: (a) administering to a subject a contrast agent comprised of an essentially water-insoluble metal-cation salt of an anionic polymer, wherein the metal has an atomic weight greater than about 40, preferably equal to or greater than about 87, and most preferably equal to or greater than about 137; and (b) performing the x-ray diagnostic procedure on said subject.

The contrast agents are administered to humans and animals in order to improve the x-ray radiation absorption of different parts of the body such as cavities and soft tissues of various organs and blood vessels. In this application the water-insoluble metal salt is preferably made available in a finely divided form suspended in a physiologically acceptable medium for administration to the patient for radiological examination. The administration of the contrast agent is conducted by methods well known in the art. Intravenous, oral, intraarterial, intracatheter and rectal routes are utilized, but others, such as subcutaneous routes are also possible.

This invention is illustrated by the following examples, which are exemplary and not intended to be limiting. All percentages, parts, etc., are by weight unless otherwise indicated.

EXAMPLE 1

This example illustrates preparation of a calcium alginate tube in 30% aqueous calcium chloride solution.

A vessel was charged with 254 parts of $CaCl_2 \cdot 2H_2O$ and 594 parts of deionized water to make a 30% aqueous $CaCl_2 \cdot 2H_2O$ solution.

Sodium alginate (Pronova Protanal LF 10/60, available from Protan Biopolymer, Inc., Portsmouth, NI-I 03801), 120 parts, was dissolved in 630 parts of deionized water to make a 16% sodium alginate solution. Since the as-received sodium alginate contained approximately 11.8% water, the actual level of dry sodium alginate in the solution was about 14.6%. The sodium alginate solution was extruded through a tubing die with the 30% $CaCl_2 \cdot 21$ $H_2O$ solution pumping through the lumen to keep the tube open. The tube was spun into a bath of 30% $CaCl_2 2H_2O$ and allowed to develop fully for over 1 hour in the bath. The product was a calcium alginate hydrogel tube, hereinafter referred to as "Example 1, 30Ca".

In the same way a calcium alginate tube was spun into a 10% aqueous $CaCl_2 \cdot 2H_2O$ solution. This product is hereinafter referred to as "Example 1, 10Ca".

EXAMPLE 2

This example illustrates preparation of a barium alginate tube.

Calcium alginate tubing (Example 1, 30Ca) was soaked in a bath of 25% aqueous KCl for 40 minutes with continuous stirring of the KCl solution. Then the tubing was transferred to a bath consisting of 75 parts of $BaCl_2 \cdot H_2O$ dissolved in 2996 parts of deionized water and left in the bath for 60 minutes while the bath was stirred continuously. The tubing was then given three 30 minute washes in deionized water. It was then soaked in a 0.15% aqueous $Na_2SO_4$ solution for 10 minutes with continuous stirring. This was followed by three more 30-minute washes in deionized water. The product was a barium alginate tube.

EXAMPLE 3

This example illustrates the preparation of a strontium alginate tube.

Calcium alginate tube (Example 1, Ca10) was soaked in a bath of 25% aqueous KCl for 40 minutes with continuous stirring of the KCl solution. Then the tube was transferred to a bath consisting of 129 parts of $SRCl_2 \cdot 6H_2O$ dissolved in 301 parts of deionized water and left in the bath overnight. The tube was then washed in deionized water to yield a strontium alginate tube.

EXAMPLE 4

This example illustrates the preparation of a lead alginate tube.

Calcium alginate tube (Example 1, Ca10) was soaked in a bath of 25% aqueous KCl for 40 minutes with continuous stirring of the KCl solution. The tube was soaked in a bath consisting of 20 parts of lead nitrate dissolved in 380 parts of deionized water overnight and then washed with deionized water to yield a lead alginate tube.

EXAMPLE 5

This example illustrates the preparation of a paraffin rod.

Paraffin was melted at 90° C. A 0.5 cc tuberculin syringe with the shaft cut off at the zero mark was used to draw the paraffin into the syringe. The paraffin was allowed to cool to room temperature, and then the rod of solidified paraffin was extruded from the syringe.

EXAMPLE 6

This example describes preparation of a paraffin rod containing barium alginate filler.

Approximately 3 parts of sodium alginate was added to 2.5% aqueous solution of $BaCl_2$ with stirring. Mixing was continued for 1 hour and then the barium alginate powder was isolated by filtration, suspended in 100 parts of deionized water for 30 minutes, filtered again, and then dried under vacuum at 37° C.

The barium alginate powder, 2.81 parts, was mixed with 2.84 parts of molten paraffin wax in a vial. The vial was heated to 90° C. to remelt the mixture, and then it was shaken to homogenize the contents. A tuberculin syringe was used to prepare a solid rod (as in Example 5) of paraffin filled with 50% by weight of barium alginate.

EXAMPLE 7

This examples describes preparation of a paraffin rod with sodium alginate filler.

Six parts of paraffin was melted at 90° C. in a vial, and then 6 parts of sodium alginate was added and mixed into the paraffin. The mixture was reheated to 90° C., and then the vial was shaken to homogenize the contents. A tuberculin syringe was used to prepare a solid rod as described in Example 5. The product was a paraffin rod filled with 50% by weight of sodium alginate.

EXAMPLE 8

This example describes the procedure for determining radiopacities, and the results obtained.

The radiopacities were determined by Computed Tomography (CT) performed on a General Electric Syntec 3000i Scanner with the following settings:

| Voltage: | 120 KV |
| --- | --- |
| Amperage: | 160 ma |
| Scan Time: | 2.7 sec |
| Field of View: | 22 cm |
| Slice Thickness: | 1 mm |
| Reconstruction Algorithm: | Edge |
| Enhancement: | E4 |
| Analysis Settings | |
| Window: | 1800 |
| Level: | 0 |
| Magnification: | 5x |
| Region of Interest: | single pixel |

The samples for analysis were configured as tubes or rods of length 1.9–2.5 cm. The CT was taken across the tubes and rods, which were held in a Plexiglass fixture having holes which closely approximating the diameter of the sample in order to maintain linearity of the sample during the test. A tube made from C-flex was used as a control. C-flex is a commercial material with good radiopacity used to manufacture ureteral stents and other tubular medical implants.

For each sample 4 radiopacity readings were obtained at 90° intervals starting at the "12 o'clock" or top position. The data in the table below contain the readings at the four positions labeled "12 o'clock", "3 o'clock", "6 o'clock" and "9 o'clock", as well as the average of the four readings. The data are reported in hounsfield units.

| | RADIOPACITIES, HOUNSFIELD UNITS | | | | |
| --- | --- | --- | --- | --- | --- |
| | SAMPLE POSITION | | | | |
| SAMPLE | 12 O'CLOCK | 3 O'CLOCK | 6 O'CLOCK | 9 O'CLOCK | AVE. |
| C-flex Tube | 2174 | 2522 | 2875 | 2446 | 2504 |
| Lead Alginate Tube (Example 4) | 3393 | 3346 | 2500 | 3876 | 3279 |
| Barium Alginate Tube (Example 2) | 2367 | 1954 | 2227 | 2036 | 2146 |
| Strontium Alginate Tube (Example 3) | 731 | 633 | 829 | 628 | 705 |
| Calcium Alginate Tube (Example 1, 30 Ca) | 230 | 125 | 163 | 225 | 186 |
| Calcium Alginate Tube (Example 1, 10 Ca) | 114 | 84 | 78 | 144 | 105 |
| Paraffin Rod (Example 5) | 4 | 157 | 2 | 74 | 59 |
| Paraffin/Sodium Alginate Rod (Example 7) | 263 | 227 | 297 | 291 | 270 |
| Paraffin/Barium Alginate Rod (Example 6) | 5337 | 7610 | 5484 | 5808 | 6060 |
| Air | −1036 | −985 | −1017 | | −1013 |
| Plexiglass | 101 | 112 | | | 107 |

It is not intended that the examples presented here should be construed to limit the invention, but rather they are submitted to illustrate some of the specific embodiments of the invention. Various modifications and variations of the present invention can be made without departing from the scope of the appended claims.

What is claimed is:

1. A method for increasing the radiopacity of a medical device comprising:
   (a) providing: (i) a medical device comprising a cation salt of an anionic polymer and (ii) an aqueous solution of a water-soluble composition containing metal-cations of atomic weight greater than about 40; and
   (b) soaking said medical device in said aqueous solution for a time effective to replace at least a portion of the cations in the medical device with said metal-cations to form an essentially water-insoluble metal-cation salt of anionic polymer dispersed within said medical device, thereby obtaining a medical device with increased radiopacity.

2. The method of claim 1 wherein said medical device is selected from the group consisting of catheters, stents, cannulas, plugs and constrictors.

3. The method of claim 1 wherein said medical device is degradable in vivo.

4. The method of claim 1 wherein said medical device is non-degradable in vivo.

5. The method of claim 1 wherein the essentially water-insoluble metal-cation salt of anionic polymer is present at a minimum level of about 1% by weight on a dry basis based on the dry weight of the medical device.

6. The method of claim 5 wherein the essentially water-insoluble metal-cation salt of anionic polymer is present at a minimum level of about 10% by weight on a dry basis based on the dry weight of the medical device.

7. The method of claim 6 wherein the essentially water-insoluble metal-cation salt of artionic polymer is present at a minimum level of about 50% by weight on a dry basis based on the dry weight of the medical device.

8. The method of claim 1 wherein said anionic polymer comprises polysaccharide.

9. The method of claim 1 wherein the anionic polymer comprises at least one polymer from the group consisting of carboxylate and sulfate functionalized polymers.

10. The method of claim 6 wherein the anionic polymer comprises at least one polymer selected from the group consisting of polyacrylic acid, polymethacrylic acid, alginic acid, pectinic acid, carboxymethyl cellulose, carboxymethyl dextran, carboxymethyl starch, carboxymethyl chitosan, hyaluronic acid, heparin, heparin sulfate and chondroitin sulfate.

11. The method of claim 1 wherein said metal-cation has an atomic weight equal to or greater than about 87.

12. The method of claim 1 wherein said metal-cation has an atomic weight equal to or greater than about 137.

13. The method of claim 1 wherein the essentially water-insoluble metal-cation salt is at least one member selected from the group consisting of salts of barium, strontium, iron, copper, lead, tin, iron, gold and silver.

14. The method of claim 13 wherein said essentially water-insoluble metal-cation salt comprises a salt of barium.

15. The method of claim 13 wherein said essentially water-insoluble metal-cation salt comprises a salt of strontium.

16. The method of claim 1 wherein the essentially water-insoluble metal-cation salt of anionic polymer comprises a salt of alginic acid and at least one metal cation selected from the group consisting of cations of barium, strontium, iron, copper, lead, tin, iron, gold and silver.

17. The method of claim 16 wherein the essentially water-insoluble metal-cation salt of anionic polymer comprises barium alginate.

18. The method of claim 16 wherein the essentially water-insoluble metal-cation salt of anionic polymer comprises lead alginate.

19. The method of claim 1 wherein the minimum level of radiopacity of the medical device is about 100 hounsfield units.

20. The method of claim 19 wherein the minimum level of radiopacity of the medical device is about 300 hounsfield units.

21. The method of claim 20 wherein the minimum level of radiopacity of the medical device is about 500 hounsfield units.

22. The method of claim 21 wherein the minimum level of radiopacity of the medical device is about 700 hounsfield units.

23. The method of claim 1 wherein the anionic polymer is ionically crosslinked.

24. A medical device prepared by the method of claim 1.

* * * * *

UNITED STATES PATENT AND TRADEMARK OFFICE
CERTIFICATE OF CORRECTION

PATENT NO. : 5,702,682
DATED : December 30, 1997
INVENTOR(S) : Samuel Anthony Thompson It is certified that error appears in the above-identified patent and that said Letters Patent is hereby corrected as shown below:

Column 2, Line 33, delete first word "artionic" and insert --anionic--.

Column 2, Line 66, delete "uretheral" and insert --ureteral--.

Column 4, Line 51, "mount" should read --amount--.

Column 7, Line 11, delete the "s" in examples (typo).

Column 9, Line 10, delete "artionic" and insert --anionic--.

Signed and Sealed this

Twelfth Day of May, 1998

*Attest:*

BRUCE LEHMAN

*Attesting Officer*  *Commissioner of Patents and Trademarks*